(12) United States Patent
Meckes et al.

(10) Patent No.: US 11,083,369 B2
(45) Date of Patent: Aug. 10, 2021

(54) EYE SURGERY SYSTEM AND METHOD FOR PREPARING INTERVENTIONS WITHIN THE SCOPE OF EYE OPERATIONS

(71) Applicant: Carl Zeiss Meditec AG, Jena (DE)

(72) Inventors: Günter Meckes, Munich (DE);
Thomas Schuhrke, Munich (DE);
Karsten Laubner, Munich (DE);
Konstantinos Filippatos, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 390 days.

(21) Appl. No.: 15/996,449

(22) Filed: Jun. 2, 2018

(65) Prior Publication Data
US 2018/0344155 A1 Dec. 6, 2018

(30) Foreign Application Priority Data

Jun. 2, 2017 (DE) ...................... 10 2017 209 425.7

(51) Int. Cl.
*A61B 3/13* (2006.01)
*A61B 3/113* (2006.01)
(Continued)

(52) U.S. Cl.
CPC .............. *A61B 3/13* (2013.01); *A61B 3/0025* (2013.01); *A61B 3/113* (2013.01); *G06T 7/0014* (2013.01); *A61B 3/107* (2013.01)

(58) Field of Classification Search
CPC .... G02B 21/365; G02B 21/06; G02B 21/361; G02B 21/16; G02B 21/24; G02B 21/22;
(Continued)

(56) References Cited

U.S. PATENT DOCUMENTS

2002/0188172 A1* 12/2002 Irion ........................ A61B 1/04
600/117
2011/0153013 A1 6/2011 Moeller et al.
(Continued)

FOREIGN PATENT DOCUMENTS

DE 10 2004 055 683 B4 9/2006
EP 2 184 005 A1 5/2010
(Continued)

OTHER PUBLICATIONS

Office Action of the German Patent and Trademark Office (DPMA), and English-language translation thereof, issued in counterpart application DE 10 2017 209 425.7, to which this application claims priority, dated Mar. 19, 2018.

*Primary Examiner* — Darryl J Collins
*Assistant Examiner* — Tamara Y. Washington
(74) *Attorney, Agent, or Firm* — Falk Ewers; Ewers IP Law PLLC

(57) ABSTRACT

An eye surgery system includes an operating microscope having at least one camera, a data memory, a pattern generator, and a display apparatus. The operating microscope presents a microscope image of an eye, and the at least one camera records a camera image of the eye. The data memory stores data that represent at least one predetermined position, relative to the eye, of a trocar to be inserted into the eye. The pattern generator generates a pattern representing the predetermined position of the trocar on the basis of the data stored in the data memory and the camera image recorded by the camera, and the display apparatus overlays the pattern produced by the pattern generator on the microscope image of the eye.

6 Claims, 3 Drawing Sheets

(51) Int. Cl.
*A61B 3/00* (2006.01)
*G06T 7/00* (2017.01)
*A61B 3/107* (2006.01)

(58) Field of Classification Search
CPC .............. G02B 21/0012; G02B 21/006; A61B 1/00188; A61B 2090/372; A61B 2090/371; A61B 5/0066; A61B 3/13; B82Y 20/00; G03B 17/48; G03B 17/14
USPC ......................................................... 359/363
See application file for complete search history.

(56) References Cited

U.S. PATENT DOCUMENTS

| | | | |
|---|---|---|---|
| 2011/0230751 A1 | 9/2011 | Kersting | |
| 2012/0272801 A1* | 11/2012 | Ichihara | G01N 1/06 83/30 |
| 2013/0144260 A1* | 6/2013 | Dewoolfson | A61K 38/45 604/506 |
| 2018/0185025 A1* | 7/2018 | Gorek | A45F 5/00 |
| 2018/0299658 A1* | 10/2018 | Carrasco-Zevallos | G02B 21/22 |
| 2020/0294203 A1* | 9/2020 | Ikeda | G06T 5/003 |
| 2020/0405406 A1* | 12/2020 | Harris | A61B 46/40 |

FOREIGN PATENT DOCUMENTS

| | | |
|---|---|---|
| WO | 2010/ 064 062 A1 | 2/2010 |
| WO | 2012/ 041 349 A1 | 4/2012 |

\* cited by examiner

EYE SURGERY SYSTEM AND METHOD FOR PREPARING INTERVENTIONS WITHIN THE SCOPE OF EYE OPERATIONS

CROSS REFERENCE TO RELATED APPLICATIONS

This application claims priority to German patent application DE 10 2017 209 425.7 filed on Jun. 2, 2017, which is hereby incorporated by reference in its entirety.

TECHNICAL FIELD

The present disclosure relates to an eye surgery system and a method for preparing interventions within the scope of eye operations.

BACKGROUND

Large operative accesses are dispensed with in the age of minimally invasive surgery; this is particularly sparing for the patients. In the field of eye surgery, too, complex interventions are carried out with the aid of eye surgery microscopy systems. However, the experience of the surgeon is often decisive for the success of the operation.

In order to carry out an operation in the region of the ocular fundus, it is necessary to provide access to the eye interior to facilitate the insertion of surgical instruments into the eye. So-called trocars are usually used to this end. These are small tubes, for example made of metal, which keep the transconjunctival microincisions open during the operation and consequently facilitate the effort-free introduction of the instruments during the operation. The trocars also protect the vitreous humour base when inserting the instruments and thereby minimize the risk of retinal holes which could otherwise arise during the operation. The use of trocars can shorten the operating time, there is less trauma to the eye, and the convalescence process can be quicker as a result thereof.

The positions at which the trocars should be placed are important for the success of a surgical intervention in the eye interior and have to be determined with great accuracy. The surgeon determines these positions during the surgical intervention with the aid of marking tools, such as templates for the distance from the limbus, for example. However, this constitutes an additional work step during the operation, which increases the length of the operation and may also be a cause of errors.

Moreover, the markings indicating the positions of the trocars to be inserted cannot always be identified easily, leading to the operating conditions becoming more difficult. Since the surgeon determines the angle position for the insertion of the individual trocars visually by observing the operating field, this determination is also inaccurate and requires additional time outlay such that the operation duration furthermore increases and is not sparing for the patient.

SUMMARY

It is therefore an object of the present disclosure to provide an eye surgery system and a method for preparing an intervention within the scope of an eye operation and for carrying out an intervention within the scope of an eye operation, which facilitate a further improvement in the success of the intervention to be carried out.

According to exemplary embodiments of the present disclosure, an eye surgery system comprises an operating microscope that is configured to present a microscope image of an eye and that comprises a camera for recording a camera image of the eye. Moreover, the eye surgery system comprises a data memory that is provided to store data that represent at least one predetermined position of a trocar to be inserted into the eye, the trocar serving as an access to the eye interior and facilitating the insertion of the necessary instruments during a surgical intervention, to be precise relative to the eye, in particular relative to certain eye-specific features.

The eye surgery system also has a pattern generator that is configured to generate a pattern representing the predetermined position of the trocar on the basis of the data stored in the data memory and the camera image recorded by the camera such that the exact position of each of the trocars to be inserted and the angle position can be determined prior to the surgical intervention. Here, the data can be recorded manually by the physician during an examination, can be added to a data processing apparatus, and can be transmitted to the eye surgery system. However, it is also possible to use a diagnostic system, by which the position of the trocar can be determined with the aid of a mathematical algorithm.

The eye surgery system also comprises a display apparatus that is configured to overlay the pattern produced by the pattern generator on the microscope image and/or the camera image of the eye such that the exact positions of the trocars to be inserted are visualized and made available to the surgeon. The overlay can also be generated by a controller, which is part of a so-called eye tracker. The image of the eye recorded by the camera is displayed on the display apparatus with an overlay of the pattern produced by the pattern generator such that the exact position of the trocars to be inserted can be visualized pictorially. The patterns of the positions for the trocars displayed on the image then correspond to the exact positions of the trocars to be inserted.

By way of example, the operating microscope can comprise one, two, or more objective lenses and one or more individual eyepieces or pairs of eyepieces. The camera of the operating microscope, which is suitable for recording a camera image of the eye to be operated, can be arranged in a beam path of the operating microscope and, for example, can receive light, which has passed through an objective lens of the microscope, for producing an image of the eye.

According to an exemplary embodiment of the present disclosure, the display apparatus can have an image projector to be able to superimpose a presentation of marking patterns into the beam path to the eyepiece of the operating microscope.

According to a further exemplary embodiment of the disclosure, the display apparatus can comprise a head-mounted apparatus ("head mounted display") and/or a monitor which can be carried by a console or a stand. However, the display apparatus can also be contained in so-called "smartglasses."

What this solution easily achieves is that the accuracy when using trocars as accesses for passing eye-surgical instruments into the eye interior is improved in comparison with previous procedures, with a significantly reduced time outlay, which is of great importance in the field of eye surgery, in particular, because the human eye is one of the most sensitive organs.

Since it is also possible to determine more accurately than in the related art the angle position denoting the alignment of the trocar to be inserted in the circumferential direction, to be precise in relation to eye-specific features, such as blood arteries, for example, which are determined prior to the surgical intervention, it is possible to increase the operation success. Additionally, the risk of iatrogenic retinal damage is lower than previously as a result of using the eye surgery system according to an exemplary embodiment the disclosure.

According to a further exemplary embodiment of an eye surgery system according to the present disclosure, the latter comprises an input apparatus for entering the data stored in the data memory. The eye surgery system can have a diagnostic system, which may be embodied separately from the imaging system. The diagnostic system can contain a camera for recording the image of the eye to be operated and an interface for outputting the image, in particular in such a format that the image is immediately suitable to be entered into the input apparatus and processed by an image processing apparatus.

According to a further exemplary embodiment of the disclosure, the pattern generator of the eye surgery system is further configured to generate a pattern representing an outline of a limbus, for example, on the basis of the camera image recorded by the camera. However, it is also possible to generate further patterns, which may display further eye-specific features, in particular specific biometric parameters of the eye, and the positions of blood arteries, for example.

According to an exemplary embodiment of the present disclosure, the trocar to be inserted has a substantially tube-shaped form. However, the trocar may also have a semi-circular shape to simplify the guidance of an operating instrument to be inserted into the eye interior, the semi-circular shape allowing fast and simple removal of the trocar after completion of the surgical intervention. By way of example, a trocar that finds use in eye surgery can be produced from metal. However, the trocar can also be made from ceramic, plastic, or polymers.

Further, the eye surgery system according to a further exemplary embodiment of the disclosure can be used to determine the accurate position of a plurality of trocars to be inserted, the trocars being able to have dimensions that differ from one another and optically perceivable labels that differ from one another, in particular different colors. Consequently, appropriate pattern marking elements can be produced and different trocars with different dimensions and forms can be used. As a result of this pictorially presentable distinction of the trocars from one another, the risk of errors during use within the scope of a surgical intervention is reduced because the individual trocars to be inserted have distinguishing features that exactly correspond to the pattern created by the pattern generator in advance. Consequently, the operating time can be shortened. For example, the pattern corresponding to a particular trocar is generated such that it appears on the display apparatus in a color which is perceived by the user as a color which is the same or similar to the color of this particular trocar when directly viewed by the user. Further, this pattern is perceived by the user to have a color different from other trocars when directly viewed by the user, wherein these other trocars have themselves colors, sizes, and geometries different from the particular trocar.

According to exemplary embodiments of the disclosure, a method for preparing an intervention within the scope of an eye operation is provided, the method comprising the following method steps: determining a position pre-surgery, at which a trocar should be inserted into an eye; producing an image of the eye; and displaying the determined position at which the trocar should be inserted into the eye in overlaid fashion on the produced image.

As a result of such a pre-surgical method, it is possible to plan the positions of the trocars to be inserted in advance, even before the surgical intervention by virtue of specific biometric features being used to determine the best possible position of a trocar to be inserted later. Here, it is possible to determine specific eye features, such as an outline of the limbus and the angle of rotation of the eye relative to a reference image. Then, the positions determined thus can be transferred to the operating microscope before the surgical intervention, wherein the previously determined positions, at which the trocars are to be inserted, can be visualized in overlaid fashion on a produced image of the eye.

According to an exemplary embodiment, the determined positions, at which at least one or more trocars should be inserted, can be stored and displayed during the surgical intervention with a display apparatus.

According to a further exemplary embodiment, pre-defined patterns of positions for trocars are used and/or new patterns of positions are defined when determining positions of the trocars, the positions being able to be stored in a database and used in subsequent interventions.

According to an exemplary embodiment of the present disclosure, a method for carrying out an intervention within the scope of an eye operation is provided, the method including the following method steps: determining a position at which a trocar should be inserted into an eye; producing an image of the eye; presenting the determined position at which the trocar should be inserted into the eye in overlaid fashion on the produced image; and introducing the trocar into the eye at the determined position illustrated in the image.

According to an exemplary embodiment of the present disclosure, producing the image of the eye and presenting the determined position in overlaid fashion on the produced image are implemented with the aid of an operating microscope. However, it is also conceivable that the image of the eye is produced by an apparatus connected to the operating microscope and the image is transmitted to the operating microscope during the surgical intervention.

According to an exemplary embodiment of the present disclosure, the method for carrying out an intervention within the scope of an eye operation can furthermore comprise: producing a plurality of pattern elements, wherein each pattern element denotes the position of a trocar relative to the eye, and wherein the plurality of pattern elements are presented in different colors.

According to a further exemplary embodiment of the present disclosure, a plurality of trocars can be inserted in the method for carrying out an intervention within the scope of an eye operation, the trocars having different colors corresponding to the colors of the pattern elements and/or different perceivable labels such that the surgeon can insert a specific trocar type at a certain position without further mental steps, further reducing the operating time.

In a typical exemplary embodiment of a method according to an exemplary embodiment of the disclosure for carrying out an intervention within the scope of an eye operation, the entire pattern and/or the individual pattern elements can be activated or deactivated during the surgical intervention. Consequently, the surgeon can successively introduce the trocars by virtue of only the respective pattern element being able to be superimposed, such that the surgeon can concentrate only on the respective trocar to be inserted.

BRIEF DESCRIPTION OF THE DRAWINGS

The disclosure will now be described with reference to the drawings wherein.

DESCRIPTION OF EXEMPLARY EMBODIMENTS

Figure 1:
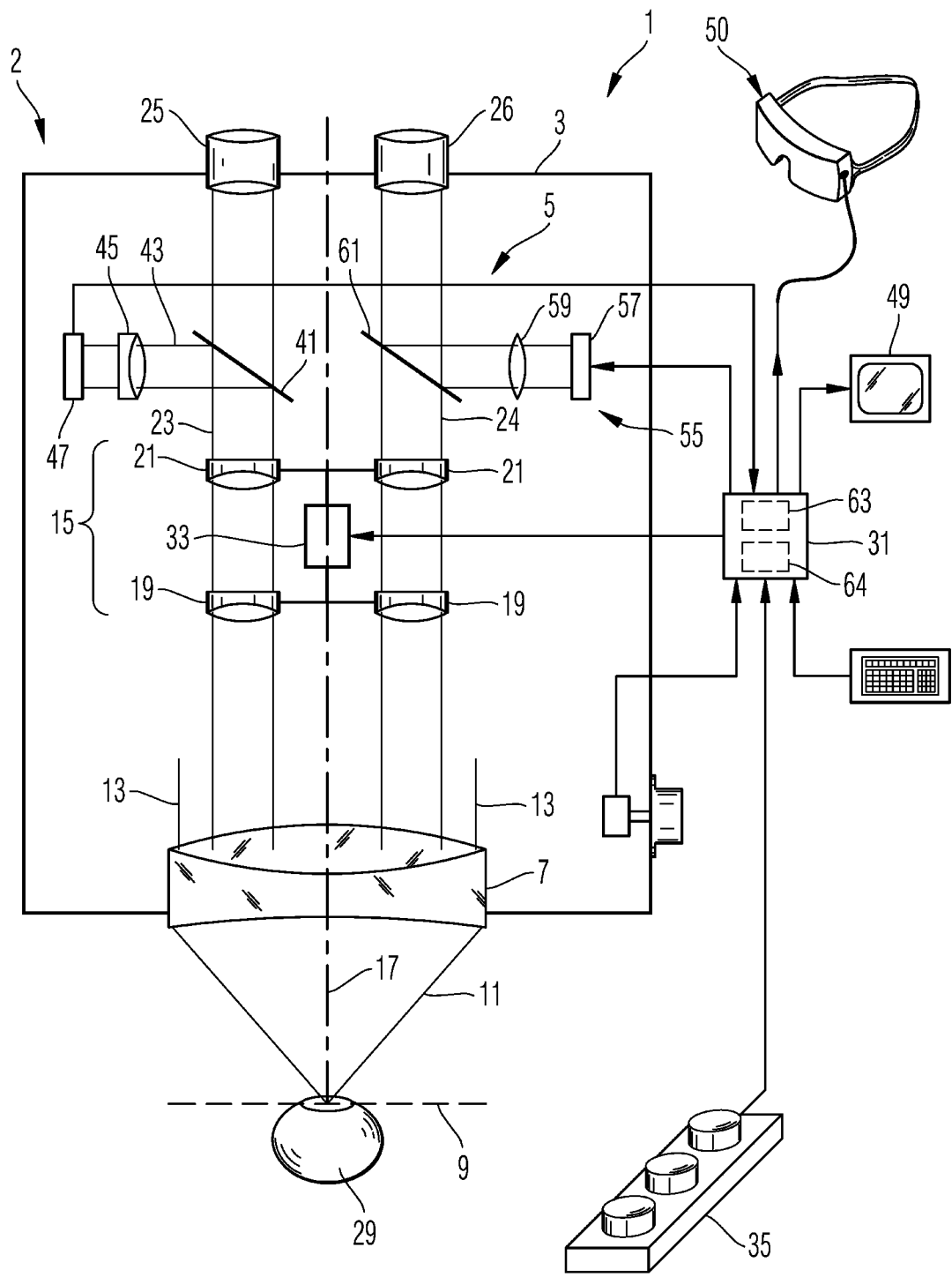
FIG. 1 shows a simplified schematic illustration of an eye surgery system according to an exemplary embodiment.

FIG. 1 schematically illustrates an eye surgery system 1 according to an exemplary embodiment of the disclosure. The system comprises an operating microscope 2 that has a housing body 3, in which a microscopy optical unit 5 is accommodated. The microscopy optical unit 5 comprises a microscopy objective lens 7, which converts an object-side divergent beam 11 emanating from an object plane 9 of the objective lens 7 into an image-side parallel beam 13. From the latter, a zoom system 15 of duplicate design having lens element groups 19 and 21 that are displaceable along an optical axis 17 of the objective lens 7 takes out two partial beams 23 and 24 that are fed to eyepieces 25 and 26, respectively, into which the surgeon can look with their left and right eye to observe an image of the object plane 9. The lens element groups 19 and 21 of the zoom system 15 can be displaced by a motor 33 and hence it is possible to actuate a change in a magnification of the microscopy optical unit 5. Commands for actuating the motor 33 are received by a controller 31 from, e.g., a control panel 35 with pushbuttons, which are actuated by the foot of the surgeon or the person carrying out the intervention.

The operating microscope 2 further comprises a camera 47, by which a camera image of the eye 29 is recorded, and a semi-transparent mirror 41, which is arranged in the partial beam 23 in order to decouple a beam 43 therefrom, the beam being guided via an adapter optical unit 45 onto a chip of the camera 47 in such a way that an image of the object plane 9 is formed on the chip. Images recorded by the camera 47 are read by the controller 31 and displayed on a screen 49. Hence, the same image of the object plane 9, as perceived by an observer when looking through the eyepieces 25, 26, is visible on the screen 49.

The same image that is displayed on the screen 49 is furthermore also displayed on a head mounted display 50 as a display apparatus, the surgeon being able to wear the head mounted display on the head to observe the same image as they are able to perceive when looking in the eyepieces 25 and 26 or when looking at the screen 49.

The eye surgery system 1 further comprises a projector 55 having a display apparatus 57, for example an LCD display, a projection optical unit 59 and a semi-transparent mirror 61. The semi-transparent mirror 61 is arranged in the partial beam 24 and the mirror couples a pattern that is displayed by the display apparatus 57 and projected by the optical unit 59 into the partial beam 24 in such a way that the pattern is perceived in overlaid fashion on the image of the object plane 9 when looking into the eyepieces 25, 26 or at the head mounted display 50 or when looking at the display 49.

The pattern displayed by the display apparatus 57 is produced by a pattern generator 64 of the eye surgery system 1 according to an exemplary embodiment of the disclosure in the controller, wherein the controller 31 also overlays this pattern on the image illustrated on the screen 49. The pattern generator 64 is configured to generate a pattern representing the predetermined positions of one or more trocars 70 to be inserted, the pattern being based on data stored in a data memory 63 of the eye surgery system 1 and the camera image recorded by the camera 47. The data that represent at least one predetermined, planned position of the at least one trocar to be inserted into the eye relative to eye-specific parameters representing the biometric data of the eye to be treated are stored in the data memory 63 of the eye surgery system 1. These stored data are entered into the pattern generator 64 via a controller 31 with an input apparatus to specify the exact position of the trocar 70.

Figure 2:
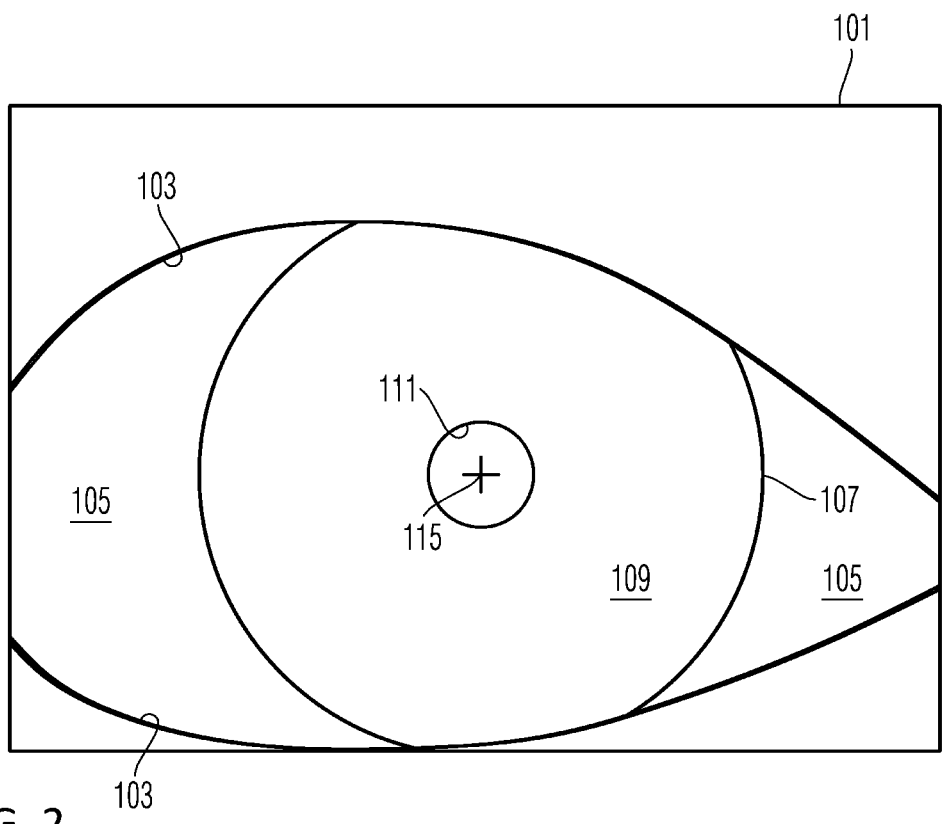
FIG. 2 shows a schematic illustration of an image of a patient's eye recorded by the eye surgery system of FIG. 1.

The controller 31 is part of a so-called eye tracker, the controller 31 having a software module that analyses the images recorded by the camera 47 for the implementation of the eye tracker. A representative illustration of such an image 100 is shown in FIG. 2. The eyelids 103, sclera 105, an outer edge 107 of an iris 109 and an inner edge 111 of the iris 109 can be identified in the image 101. The software module 63 analyses the image and the geometric center of the largest contiguous dark region, denoted by reference sign 115 in FIG. 2, is ascertained. Consequently, it is possible to ascertain the center 115 of the iris in the coordinates of the image 101 with the aid of the eye tracker. Consequently, the pattern for the insertion of the trocars on the eye can be overlaid with great accuracy in real-time during the surgical intervention. Typically, an artery pattern of the sclera 105 is used to produce a pattern for the insertion of the trocars with the aid of the eye tracker.

Figure 3:
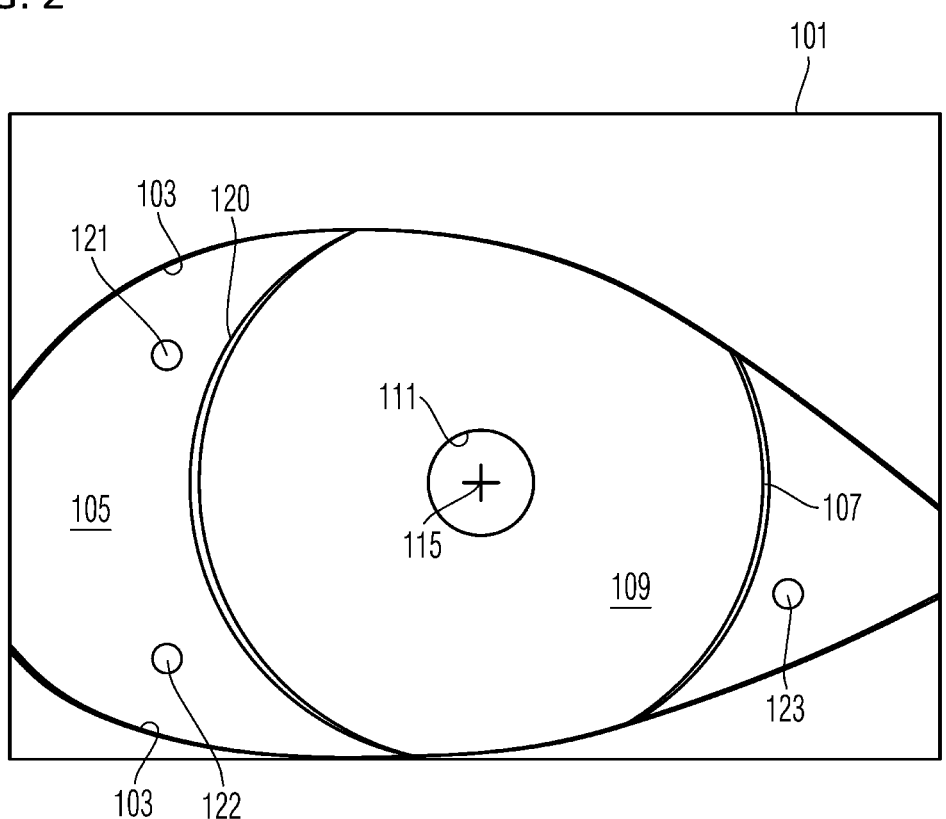
FIG. 3 shows a schematic illustration of an image corresponding to the image of FIG. 2, in which a marking pattern is superimposed as an assistance for inserting trocars into the eye to be operated.

FIG. 3 shows the microscopic image of the object plane (see FIG. 2), on which the pattern produced by the pattern generator 64 has been overlaid. The pattern includes a multiplicity of small rings 121, 122, 123 as pattern marking elements, which represent the position of a trocar to be inserted. The pattern also schematically represents an outline of the limbus 120, which serves as an orientation aid for determining the positions of the individual trocars to be inserted. By way of example, when planning the trocar positions, the distance from the limbus and also the angle position of the respective trocar to be inserted is predetermined, for example in relation to the iris.

Figure 4:
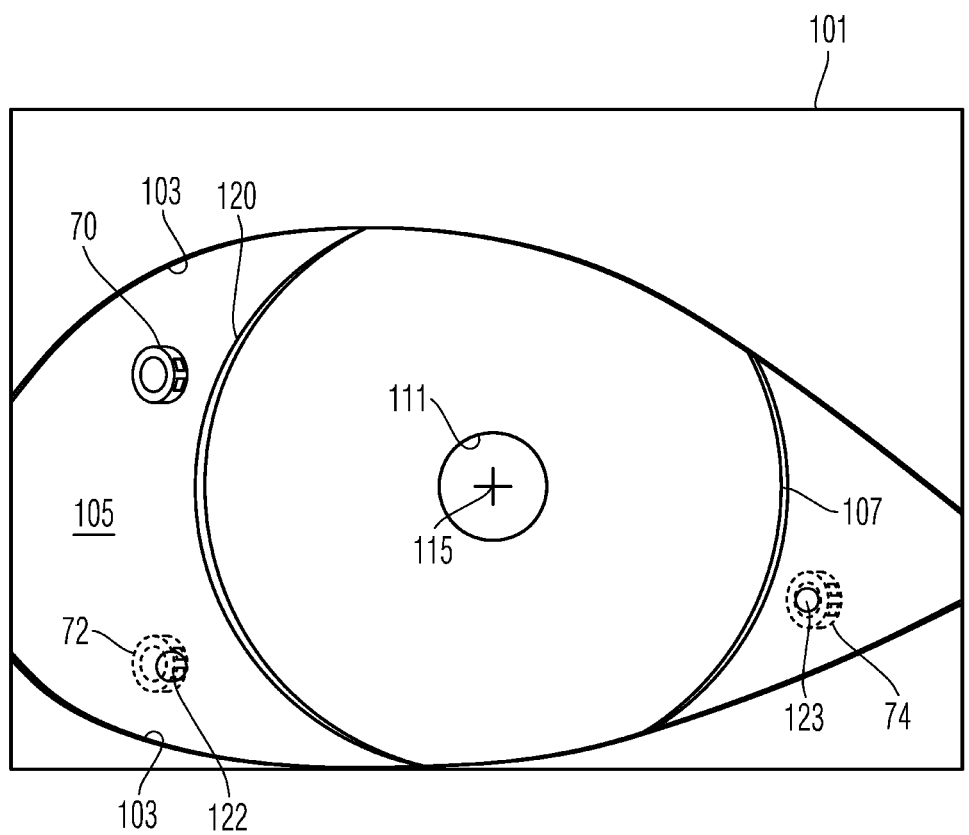
FIG. 4 shows a schematic illustration of an image corresponding to the image of FIG. 3, in which an inserted trocar is illustrated.

The next FIG. 4 shows the microscopic image of the object plane according to FIG. 3, wherein a trocar 70 that is inserted into the eye during the intervention is illustrated. It is understood that the further pattern marking elements 122, 123 serve as an orientation for the insertion of the further trocars 72, 74, which are schematically illustrated using dashed lines, wherein the insertion thereof is implemented in a subsequent method step. It should be noted here that the pattern marking elements 121, 122, 123 can be labelled using different colors such that different trocars can also be inserted. The inserted trocar 70 schematically illustrated here has a substantially round form, with other forms also being possible for a better distinction between the trocars 70, 72, 74 to be inserted.

The method according to an exemplary embodiment of the disclosure for planning and determining positions of trocars on the basis of predefined patterns or partial patterns and the eye surgery system according to an exemplary embodiment of the disclosure develop new intraoperative displays relating to the exact position for the insertion of trocars and the exact planning of these positions still before the surgical intervention.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An eye surgery system comprising:
   an operating microscope configured to present a microscope image of an eye, the operating microscope including at least one camera configured to record a camera image of the eye;
   a data memory for storing data representing at least one predetermined position of a trocar to be inserted into the eye, the at least one predetermined position being determined relative to the eye;
   a pattern generator configured to generate a pattern representing the predetermined position of the trocar on the basis of the data stored in the data memory and the camera image recorded by the camera; and
   a display apparatus configured to overlay the pattern generated by the pattern generator on at least one of the microscope image of the eye or the camera image of the eye.

2. The eye surgery system according to claim 1, further comprising an input apparatus for entering the data stored in the data memory.

3. The eye surgery system according to claim 1, wherein the pattern generator is further configured to generate a pattern representing an outline of a limbus on the basis of the camera image recorded by the camera.

4. The eye surgery system according to claim 1, wherein the trocar is substantially tubular.

5. The eye surgery system according to claim 1, further comprising:
   a plurality of trocars,
   wherein the plurality of trocars have at least one of pairwise different dimensions from one another or pairwise different optically perceivable labels from one another, and
   wherein the plurality of trocars are provided for different applications.

6. The eye surgery system according to claim 5, wherein the pairwise different optically perceivable labels from one another have different colors.

* * * * *